United States Patent [19]

Harandi et al.

[11] Patent Number: 4,788,365
[45] Date of Patent: Nov. 29, 1988

[54] HIGH OCTANE GASOLINE AND DISTILLATES FROM OXYGENATES

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 130,256

[22] Filed: Dec. 8, 1987

[51] Int. Cl.[4] .................... C07C 1/20; C07C 2/00
[52] U.S. Cl. .................... 585/312; 585/301; 585/303; 585/313; 585/314; 585/315; 585/316; 585/469; 585/640
[58] Field of Search .......... 585/301, 303, 312, 314, 585/315, 316, 469, 640

[56] References Cited

U.S. PATENT DOCUMENTS

| | | | |
|---|---|---|---|
| 3,960,978 | 6/1976 | Givins et al. | 585/331 |
| 4,021,502 | 5/1977 | Plank et al. | 585/533 |
| 4,456,779 | 6/1984 | Owen et al. | 585/415 |
| 4,482,772 | 11/1984 | Tabak | 585/315 |
| 4,506,106 | 3/1985 | Hsia et al. | 585/312 |
| 4,542,252 | 9/1985 | Graziani et al. | 585/640 |
| 4,543,435 | 9/1985 | Gould et al. | 585/330 |
| 4,544,776 | 10/1985 | Osterburg et al. | 568/697 |
| 4,547,602 | 10/1985 | Tabak | 585/314 |
| 4,603,225 | 7/1986 | Colaianne et al. | 585/331 |
| 4,654,453 | 3/1987 | Tabak | 585/303 |
| 4,684,757 | 8/1987 | Avidan et al. | 585/331 |

Primary Examiner—A. Pal
Attorney, Agent, or Firm—Alexander J. McKillop; Michael G. Gilman; L. G. Wise

[57] ABSTRACT

An integrated process for the conversion of methanol to high octane gasoline and distillate. Methanol is converted to olefins in the presence of zeolite type catalyst. $C_4$ and $C_5$ olefin fraction is converted to MTBE and TAME in the presence of excess methanol and acid etherification catalyst. Unreacted methanol and hydrocarbons are passed to an olefins to gasoline and distillate oligomerization unit in conjunction with $C_3$, $C_6$ and $C_7$ olefins from the methanol to olefins unit whereby distillate and LPG products are produced. Gasoline products from the oligomerization unit are passed to the etherification unit whereby an ether-rich gasoline fraction is separated.

12 Claims, 1 Drawing Sheet

HIGH OCTANE GASOLINE AND DISTILLATES FROM OXYGENATES

This invention relates to a process for the production of high octane gasoline and distillates from lower alkyl oxygenates. In particular, the invention relates to an integrated process for the conversion of methanol to high octane gasoline and distillates in conjunction with the production of methyl tertiary alkyl ethers.

In recent years the petroleum industry has witnessed the development of highly effective novel processes for the synthetic production of gasoline by the conversion of methanol over zeolite type catalyst, particularly medium pore size shape selective aluminosilicate catalyst. Further technological development has broadened the range of this technology to encompass the production of olefins, distillates and aromatics, based on $C_1$ chemistry and, in particular, methanol.

The ready availability of synthetic methanol from feedstocks such as natural gas, coal and wood provide, a broad basis for the production of synthetic gasoline, distillates, olefins and aromatics. Various processes in the aforenoted field of technology are described in the following U.S. patents which are incorporated herein in their entirety by reference: U.S. Pat. Nos. 3,894,107 (Butter, et al); 3,928,483; 4,025,575; 4,252,479 (Chang, et al); 4,025,572 (Lago); 4,328,384 (Daviduk, et al); 4,547,616 (Avidan, et al); 4,450,311 (Right, et al); 3,960,978 and 4,021,502 (Plank, Rosinski and Givens); 4,150,062, 4,211,640 and 4,227,992 (Garwood, et al).

Paralleling the technological development of methanol to olefins, gasoline and distillate processes has been the development of processes leading to the use of methyl tertiary alkyl ethers as octane boosters in place of conventional lead additives in gasoline. The etherification processes for the production of methyl tertiary alkyl ethers, in particular methyl tertiary butyl ether (MTBE) and methyl tertiary amyl ether (TAME) have been the focus of considerable research attention to resolve certain limitations in the etherification process with respect to the opportunity to drive the equilibrium dependent etherification reaction to completion by conducting etherification in the presence of excess methanol. It is known that recovering unreacted methanol by conventional separation and extraction techniques imposes severe economic burdens on the etherification process. Recognizing the feedstock commonality (methanol) for the synthetic production of gasoline as well as the production of methyl tertiary alkyl octane boosting ethers research workers have endeavored to combine these processes in a manner to provide a synergistically beneficial integrated process.

Accordingly, it is an object of the present invention to provide an integrated process for the production of synthetic gasoline and distillates wherein the gasoline fraction thereof is rich in octane boosting ethers.

Another object of the present invention is to provide an integrated process for the manufacture of synthetic gasoline and distillate from lower oxygenates in conjunction with the manufacture of octane improving ethers in improved yield.

Yet another object of present invention is to provide a process for the manufacture of methyl tertiary alkyl ethers in the presence of a large excess of methanol by a process integration with methanol to olefins, gasoline and distillate technology.

SUMMARY OF THE INVENTION

It has been discovered that the process for the conversion of lower oxygenates, such as methanol, to olefins in contact with zeolite catalyst followed by the oligomerization of olefins to gasoline and distillate, also in the presence of zeolite catalyst, can be integrated with the process for the production of methyl tertiary butyl ether and methyl tertiary amyl ether. In the integrated process iso-olefins for the etherification reaction are provided from the oxygenates to olefins conversion process. Etherification of iso-olefins is conducted in the presence of a large excess of methanol. It has been discovered that following etherification the excess methanol, after separating an ether rich gasoline fraction, can be passed to the oligomerization process for conversion to gasoline and distillate. In turn, the gasoline fraction from oligomerization is passed to the etherification process which enhances the subsequent separation of methanol in the etherification effluent and leads to a gasoline fraction rich in octane boosting methyl tertiary butyl ether and methyl tertiary amyl ether. Methanol can be utilized as the only feedstream to the integrated process thereby providing a highly advantageous process where the feedstock is easily derived from plentiful supplies of natural gas, coal and wood.

More particularly, the present invention describes an integrated process for the conversion of methanol to high octane gasoline and distillate, comprising the steps of:

(a) contacting oxygenated hydrocarbon feed with solid conversion catalyst such as medium pore size shape selective zeolite type catalyst having the structure of ZSM-5 in a conversion zone under oxygenate conversion conditions to produce an effluent stream comprising a major portion of olefinic hydrocarbons wherein said catalyst has a moderately low Bronsted acid activity;

(b) fractionating said effluent stream to produce olefinic component streams comprising $C_2$-, $C_3$, $C_4$ and $C_5$, $C_6$ and $C_7$, $C_8+$ hydrocarbons;

(c) passing said $C_3$, $C_6$ and $C_7$ olefinic streams to an olefins to gasoline and distillate oligomerization zone under oligomerization conditions in contact with medium pore size shape selective zeolite type catalyst having the structure of ZSM-5 whereby $C_5+$ gasoline and distillate are produced;

(d) passing a hydrocarbon feedstream comprising a portion of step (c) $C_5+$ gasoline, step (b) olefinic component hydrocarbon streams $C_4$ and $C_5$ and, optionally, a portion of $C_8+$ in conjunction with a methanol feedstream to an etherification zone in contact with an acid etherification catalyst under etherification conditions whereby, after separation, high octane ether rich gasoline is produced and a stream comprising unreacted methanol and $C_4$ and $C_5$ hydrocarbons;

(e) passing step (b) stream comprising unreacted methanol and $C_4$ and $C_5$ hydrocarbons to step (c) oligomerization zone for conversion to gasoline and distillate.

In the aforenoted process, the step (d) methanol feedstream comprises a large stoichiometric excess of methanol based on the $C_4$ and $C_5$ iso-olefins in step (d) hydrocarbon feedstream.

DETAILED DESCRIPTION OF THE INVENTION

Figure 1:
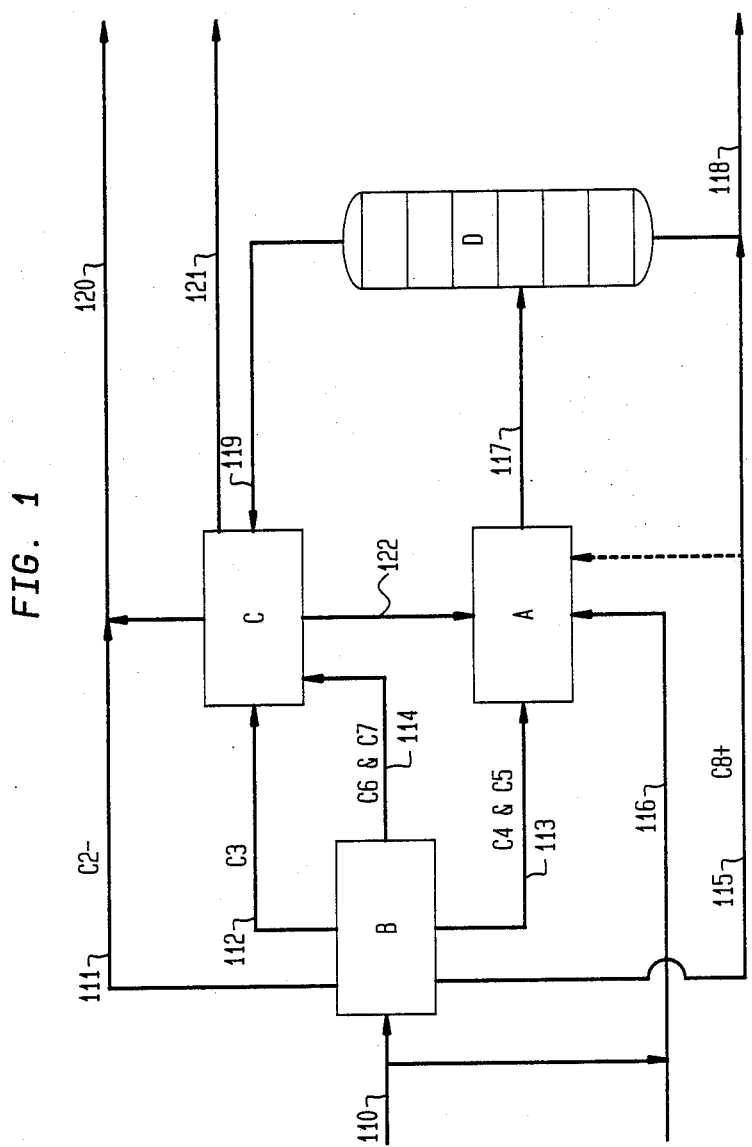
FIG. 1 is a process flow schematic of the integrated process of the present invention.

In the preferred embodiment of the instant invention the principal components of known processes are integrated in a manner providing a highly advantageous and surprising advancement in refinery technology leading to the production of high octane gasoline and distillate. Known processes are combined in a unique configuration that provides enhancement of the performance of component processes as well as achieving surprising advantages for the integrated process. The processes integrated include etherification to produce MTBE and TAME, the conversion of methanol to olefin, known as the MTO process and the conversion of olefins to gasoline and distillate, known as the MOGD process. The MTO and MOGD processes are closely related processes employing medium proe size shape selective zeolite type catalyst whose operating conditions are selected to shift the conversion reaction toward the production of olefins, in the case of MTO and the conversion of olefins to gasoline and distillate in the case of MOGD. These known processes are discussed further herein. However, in FIG. 1, the fully integrated process of the present invention incorporating these individual processes is presented in a schematic drawing.

Referring now to FIG. 1, the present invention involves the integration of etherification reaction unit A with methanol-to-olefins unit B and olefins to gasoline and distillate unit C. Separation unit D links the etherification process and the MOGD unit. The reaction conditions in etherification, methanol-to-olefins and olefins to gasoline and distillate processes are essentially those encompassing the range of conditions under which these known processes are conventionally conducted as described hereinafter.

In FIG. 1, the feedstream 110 to the MTO unit comprises light oxygenated hydrocarbons such as dimethyl ether or methanol. The feedstream, preferably methanol, is fed to the catalytic reactor of the MTO unit containing medium pore size shaped selective metallosilicate catatlyst, such as aluminosilicate, preferably ZSM-5, with an average alpha value of about 1 to 15, but preferably between 3 to 8. The reactor may be a fixed or fluid bed reactor but preferably a fluid bed reactor wherein catalyst is oxidatively regenerated in a separate vessel. Conversion of methanol to olefins is achieved at temperatures between 470°–515° C. and pressures of 220–350 kPa.

In the present invention the MTO unit B effluent stream is separated to provide a $C_2-$ stream 111, $C_3$ stream 112, a $C_4$ and $C_5$ stream 113, $C_6$ and $C_7$ 114 and $C_8+$ stream 115. The $C_4$ and $C_5$ stream 113 is passed to etherification unit A along with methanol feedstream 116 and, optionally, a portion of the $C_8+$ stream. Etherification of the $C_4$ and $C_5$ stream, comprising isobutylene and isoamylene, with methanol is achieved under moderate conditions in the presence of an acid resin catalyst.

The reaction of methanol with isobutylene and isoamylenes at moderate conditions with a resin catalyst is known technology, as provided by R. W. Reynolds, et al in *The Oil and Gas Journal*, June 16, 1975, and S. Pecci and T. Floris, *Hydrocarbon Processing*, December 1977. An article entitled "MTBE and TAME-a Good Octane Boosting Combo," by J. D. Chase, et al, *The Oil and Gas Journal*, Apr. 9. 1979, pages 149–152, discusses the techology. A preferred catalyst is a bifunctional ion exchange resin which etherifies the isomerizes the reactant streams. A typical acid catalyst is Amberlyst 15 sulfonic acid resin.

Processes for producing and recovering MTBE and other methyl tertiary alkyl ethers form $C_4$–$C_7$ isolefins are known to those skilled in the art, such as disclosed in U.S. Pat. Nos. 4,544,776 (Osterburg, et al) and 4,603,225 (Colaianne, et al). Various suitable extraction and distillation techniques are known for recovering ether and hydrocarbon streams from etherification effluents.

Referring again to FIG. 1 the etherification effluent stream 117 which comprises $C_5+$ gasoline, MTBE, TAME, unreacted methanol and unreacted olefins, is passed to fractionation separator D. From the fractionation separator a bottom stream 118 is separated which comprises an ether rich high octane gasoline. The overhead stream from the separator 119, comprising unreacted methanol plus $C_4$ and $C_5$ hydrocarbons is passed to the olefins to gasoline and distillate (MOGD) unit C. In MOGD unit C olefins are oligomerized and methanol converted to produce gasoline, distillate, LPG and lighter hydrocarbons. The oligomerization products are separated into an LPG and lighter stream 120, distillate stream 121, and gasoline stream 122. Gasoline stream 122 is passed to the etherification unit in conjunction with the aforenoted streams 113, 116 and, optionally, a portion of 115.

Operating details for typical MOGD units are disclosed in U.S. Pat. Nos. 4,456,779; 4,497,968 (Owen, et al) and 4,433,185 (Tabak) incorporated herein by reference.

An advantageous feature of the present invention involves the etherification of iso-olefins, such as isobutylene and isoamylene in the presence of a large excess of methanol so as to shift the equilibrium of the etherification reaction favorably toward the formation of ethers. Separation of unreacted methanol is uniquely accomplished in separator D of FIG. 1, augmented by $C_4$ and $C_5$ hydrocarbons fed to the etherification unit in stream 122. Since the fractionation of methanol in separator D occurs as an azeotrop with hydrocarbons, the presence of added hydrocarbon provides for an enhancement in methanol separation. Further, the recovery of methanol is avoided since the unreacted methanol from etherification is passed to the MOGD unit for conversion to olefins, gasoline and distillate.

The catalyst useful in the practice of the instant invention in the conversion of methanol to olefins and in the conversion of olefins to gasoline and distillate belongs to a group of related zeolites. Recent developments in zeolite technology have provided a group of medium pore siliceous materials having similar pore geometry. Most prominent among these intermediate pore sized zeolites is ZSM-5, which is usually synthesized with Bronsted active sites by incorporating a tetrahedrally coordinated metal, such as Al, Ga, or Fe, within the zeolytic framework. These medium pores zeolites are favored for acid catalysis; however, the advantages of ZSM-5 structures may be utilized by employing highly siliceous materials or crystalline metallosilicate having one or more tetrahedrally species having varying degrees of acidity. ZSM-5 crystalline structure is readily recognized by its x-ray defraction pattern, which is described in U.S. Pat. No. 3,702,866, (Argauer, et al), incorporated by reference.

While the invention has been described by reference to particular embodiments, there is no intent to limit the inventive concept as set forth in the following claims:

What is claimed is:

1. An integrated process for the conversion of methanol to high octane gasoline and distillate, comprising the steps of:
   (a) contacting oxygenated hydrocarbon feed with solid conversion catalyst in a conversion zone under oxygenate conversion conditions to produce an effluent stream comprising a major portion of olefinic hydrocarbons wherein said catalyst has a moderately low Bronsted acid activity;
   (b) fractionating said effluent stream to produce olefinic hydrocarbon streams comprising, first $C_2$-olefinic stream, second $C_3$ olefinic stream, third $C_4$ & $C_5$ olefinic stream, fourth $C_6$ & $C_7$ olefinic stream and fifth $C_8+$ olefinic stream;
   (c) passing said second $C_3$ olefinic stream and said fourth $C_6$ and $C_7$ olefinic stream to an olefins oligomerization zone under oligomerization conditions in contact with medium pore size shape selective zeolite catalyst whereby $C_5+$ gasoline and distillate are produced;
   (d) passing a hydrocarbon feedstream comprising a portion of step (c) $C_5+$ gasoline, step (b) third $C_4$ and $C_5$ olefinic hydrocarbon stream in conjunction with a methanol feedstream to an etherification zone in contact with an acid etherification catalyst under etherification conditions to produce a mixture of high octaine ether-rich gasoline;
   (e) recovering a stream comprising unreacted methanol and $C_4$ and $C_5$ hydrocarbons and a stream comprising ether-rich gasoline;
   (f) passing step (e) stream comprising unreacted methanol and $C_4$ and $C_5$ hydrocarbons to step (c) oligomerization zone for conversion to gasoline and distillate.

2. The process of claim 1 wherein step (d) methanol feedstream comprise a large stoichiometric excess of methanol based on the $C_4$ and $C_5$ iso-olefins in step (d) hydrocarbon feed stream.

3. The process of claim 2 wherein the large stoichiometric excess of methanol is preferably between 2 and 100 wt % of said $C_4$ and $C_5$ iso-olefins.

4. The process of claim 1 wherein excess methanol is preferably about 10 to 30 wt %.

5. The process of claim 1 wherein said oxygenated hydrocarbon feed comprises methanol, and further comprising the step of passing a portion of step (b) fifth $C_8+$ tream to the etherification zone.

6. The process of claim 1 wherein said oxygenate conversion conditions comprise temperature between 400° and 550° C., pressure between about 100 and 500 kPa and oxygenates weight hourly space velocity between about 0.1 and 10 based on active catalyst weight.

7. The process of claim 6 wherein said oxygenate conversion conditions are preferably about 500° C., 250 kPa and 1 methanol weight hourly space velocity.

8. The process of claim 1 wherein said oligomerization conditions comprise temperature between 200° and 350° C., and pressure between 3000 and 10000 kPa.

9. The process of claim 8 wherein the temperature is preferably about 250° C. and pressure about 600 kPa.

10. The process of claim 1 wherein step (a) catalyst comprises ZSM-5 having an alpha value between 1 and 20.

11. The process of claim 1 wherein step (c) catalyst comprises ZSM-5.

12. The process of claim 1 wherein step (d) high octane ether-rich gasoline comprises gasoline rich in methyl tetriary butyl ether and methyl tertiary amyl ether.

* * * * *

UNITED STATES PATENT AND TRADEMARK OFFICE
CERTIFICATE OF CORRECTION

PATENT NO. : 4,788,365
DATED : November 29, 1988
INVENTOR(S) : Mohsen N. Harandi and Hartley Owen Page 1 of 2

It is certified that error appears in the above-identified patent and that said Letters Patent is hereby corrected as shown below:

Col. 2, lines 9-10, delete "intergrated" insert --integrated--.

Col. 3, line 8, delete "octaine" insert --octane--.

Col. 3, line 18, delete "proe" insert --pore--.

Col. 3, line 43, delete "catatlyst" insert --catalyst--.

Col. 3, line 53, insert --stream-- before 114.

Col. 4, line 2, delete "the" after etherifies insert --and--.

Col. 4, line 6, delete "form" insert --from--.

Col. 4, line 43, delete "azeotrop" insert --azeotrope--.

Col. 4, line 60, delete "pores" insert --pore--.

Col. 6, line 15, delete "tream" insert --stream--.

UNITED STATES PATENT AND TRADEMARK OFFICE
CERTIFICATE OF CORRECTION

PATENT NO. : 4,788,365

DATED : November 29, 1988

INVENTOR(S) : Mohsen N. Harandi and Hartley Owen

It is certified that error appears in the above-identified patent and that said Letters Patent is hereby corrected as shown below:

Col. 6, line 28, delete "600" insert --6000--.

Signed and Sealed this

Twenty-fourth Day of October, 1989

Attest:

DONALD J. QUIGG

Attesting Officer

Commissioner of Patents and Trademarks